(12) United States Patent
Frank et al.

(10) Patent No.: US 12,263,616 B2
(45) Date of Patent: Apr. 1, 2025

(54) APPARATUS FOR PEELING LOGS

(71) Applicant: MICROTEC S.R.L., Bressanone (IT)

(72) Inventors: Jöst Frank, Brunico (IT); Federico Giudiceandrea, Bressanone (IT)

(73) Assignee: MICROTEC S.R.L., Bressanone (IT)

( * ) Notice: Subject to any disclaimer, the term of this patent is extended or adjusted under 35 U.S.C. 154(b) by 405 days.

(21) Appl. No.: 17/876,717

(22) Filed: Jul. 29, 2022

(65) Prior Publication Data

US 2023/0041296 A1    Feb. 9, 2023

(30) Foreign Application Priority Data

Aug. 4, 2021   (IT) .......................... 102021000021089

(51) Int. Cl.
   *B27L 5/02*      (2006.01)
   *G01N 23/046*    (2018.01)
   *G01N 33/46*     (2006.01)

(52) U.S. Cl.
   CPC .............. *B27L 5/02* (2013.01); *G01N 23/046* (2013.01); *G01N 33/46* (2013.01)

(58) Field of Classification Search
   CPC .................................. B27L 5/002; B27L 5/02
   See application file for complete search history.

(56) References Cited

U.S. PATENT DOCUMENTS

| | | | |
|---|---|---|---|
| 4,246,940 A | 1/1981 | Edwards et al. | |
| 4,397,343 A | 8/1983 | Fields | |
| 5,518,052 A * | 5/1996 | Westberg | G01B 5/0035 82/170 |
| 6,116,306 A * | 9/2000 | Ely | B27L 5/022 702/167 |
| 7,147,023 B2 | 7/2006 | Hyysti | |
| 7,221,995 B2 * | 5/2007 | Hyysti | B27L 5/022 700/192 |
| 2006/0162816 A1 | 7/2006 | Hyysti | |
| 2010/0161096 A1 | 6/2010 | Giudiceandrea | |
| 2011/0069811 A1 | 3/2011 | Giudiceandrea | |
| 2011/0274239 A1 | 11/2011 | Giudiceandrea | |
| 2021/0116395 A1 | 4/2021 | Ursella et al. | |

FOREIGN PATENT DOCUMENTS

| | | |
|---|---|---|
| EP | 2202039 A1 | 10/2009 |
| EP | 2381247 A1 | 10/2011 |
| IT | 201900019454 A1 | 4/2021 |
| WO | 2005030450 A1 | 4/2005 |

* cited by examiner

*Primary Examiner* — Matthew Katcoff
(74) *Attorney, Agent, or Firm* — Chrisman Gallo Tochtrop LLC

(57) ABSTRACT

Apparatus for peeling a log (5) comprising a cutting station (3), a loading station (2) and a device (4) for transferring logs (5) from the loading station (2) to the cutting station (3), the cutting station (3), the loading station (2) and the transfer device (4), in use, interacting with each other to position the log (5) in the cutting station (3). The loading station (2) comprises a device (10) for axially rotating the log (5) about a second rotation axis (11) and a radiographic examination device (19) configured to generate, in use, radiographic scans of the log (5). An electronic unit is connected both to the radiographic examination device (19), to receive digital-format data from it relating to each radiographic scan generated by it, and to the axial rotation device (10), and which is programmed to use said digital-format data to control the operation of the transfer device (4) and/or the cutting station (3).

36 Claims, 6 Drawing Sheets

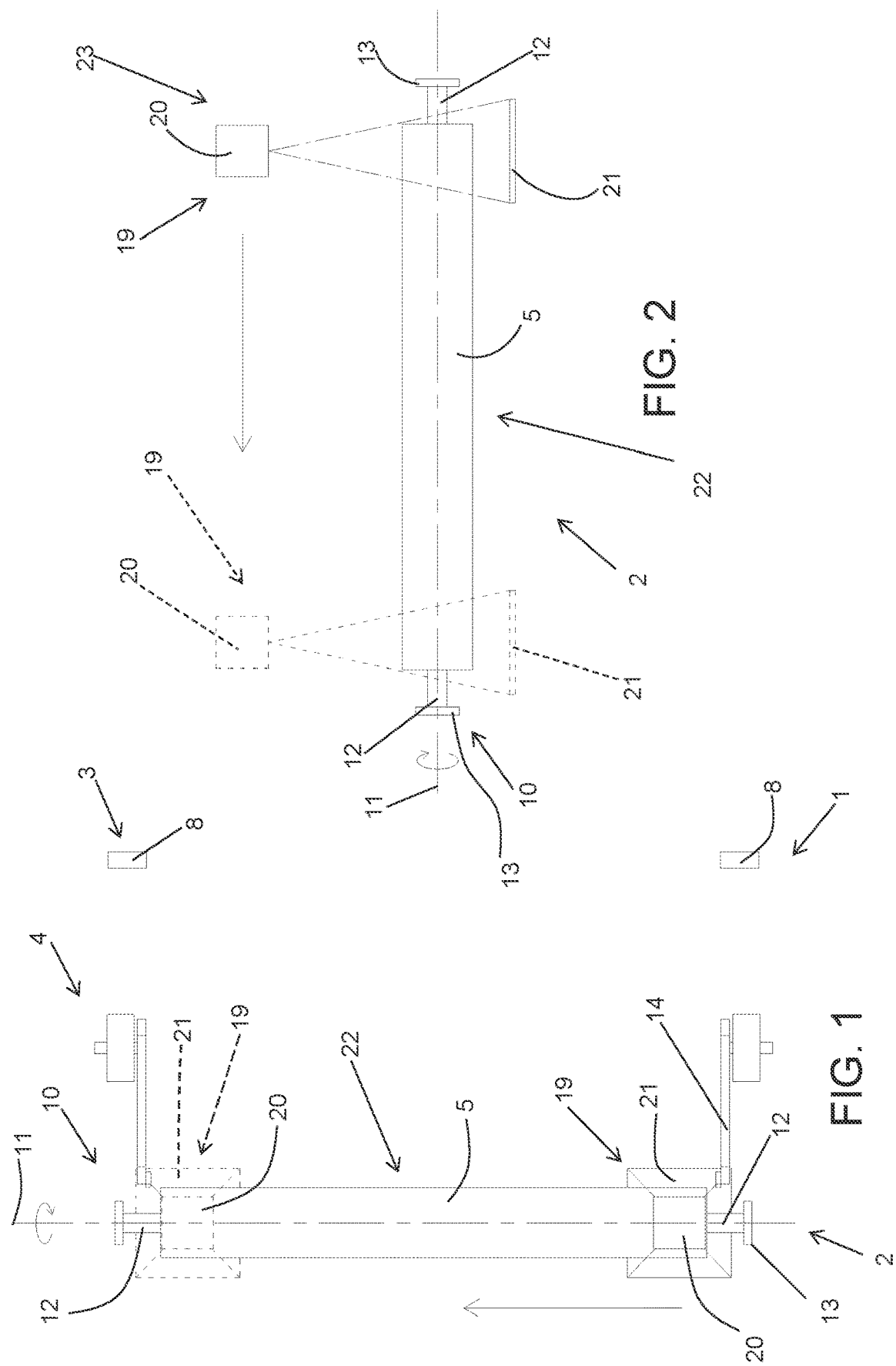

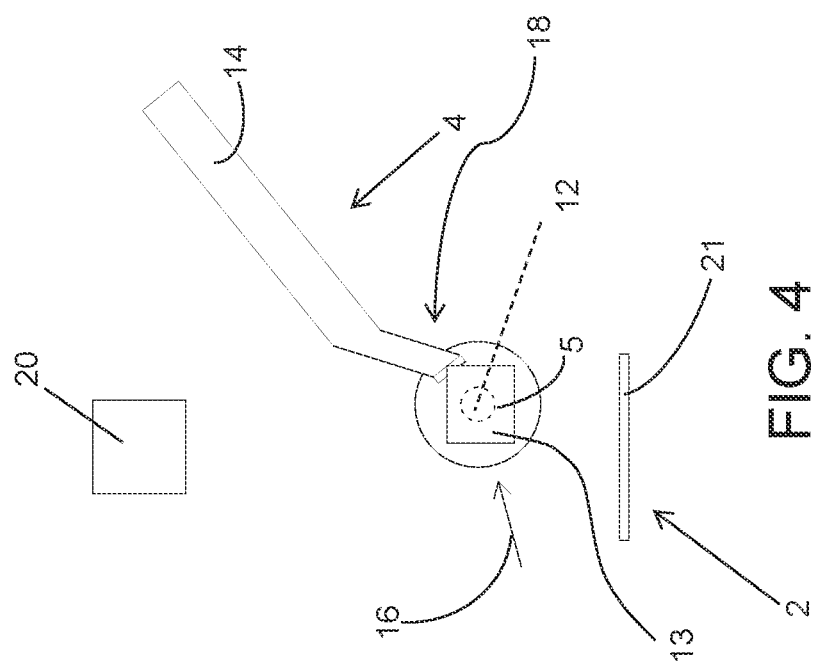
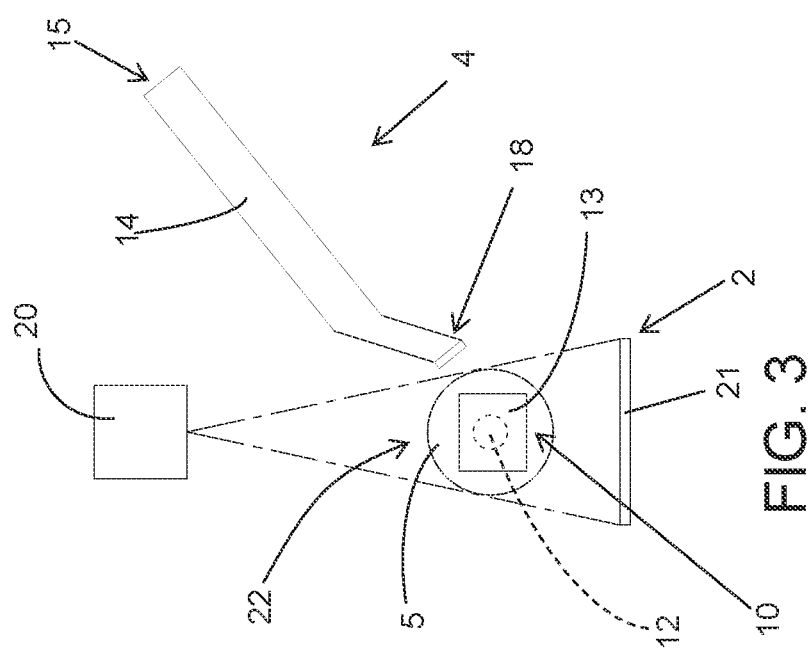

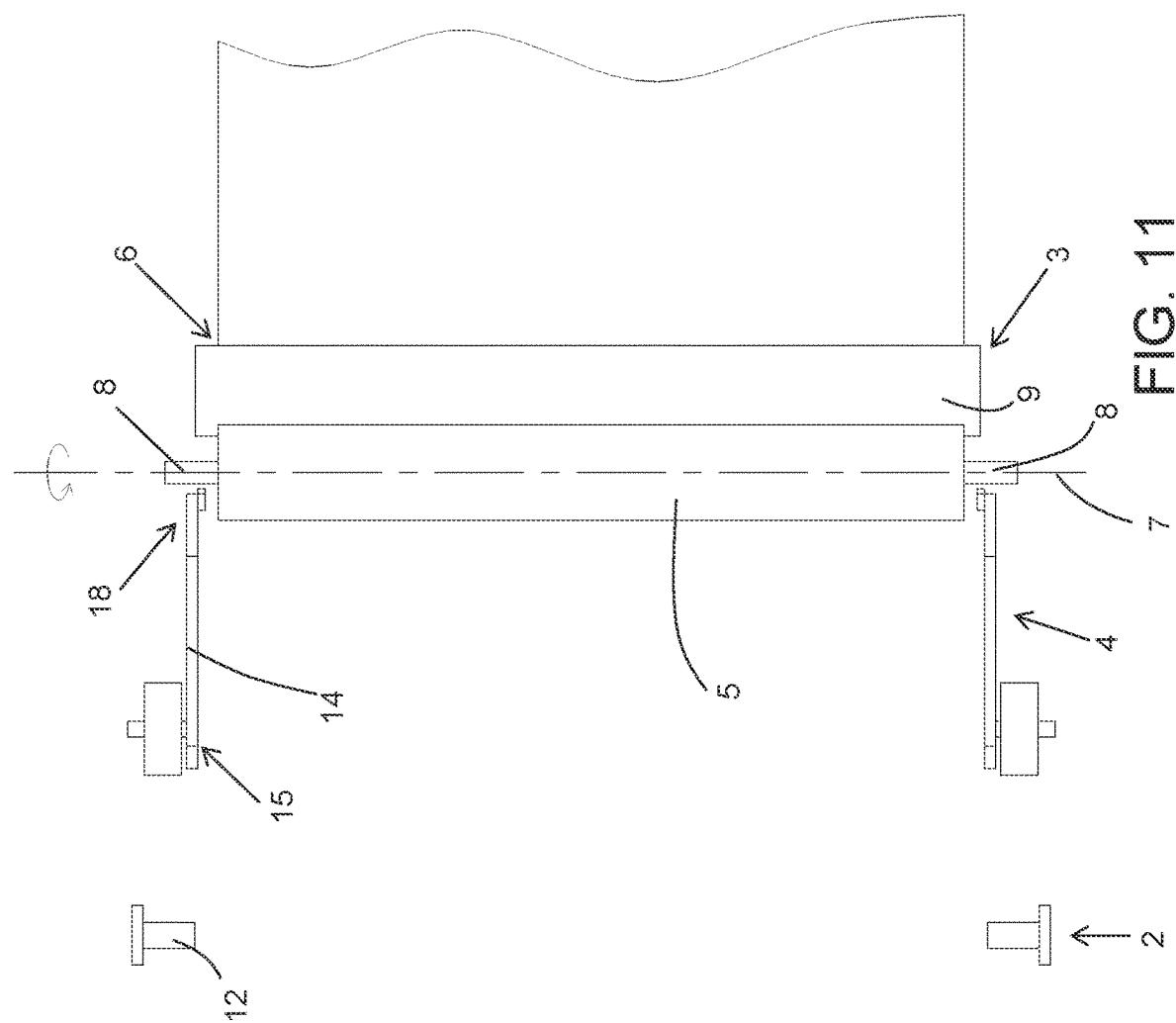

APPARATUS FOR PEELING LOGS

The present invention relates to an apparatus for peeling logs.

As is known, a peeling machine is a wood production apparatus that enables continuous veneers of a preconfigured thinness to be obtained from a tree trunk.

According to the prior art, this comprises a loading station to receive the logs that are to be cut one after the other, a cutting station, and a device for transferring one log at a time from the loading station to the cutting station.

The cutting station generally comprises two spindles capable of clamping the ends of the log between them and rotating it about a first rotation axis. Cutting is carried out by a cutting device that generally consists of a slidable blade. The blade is wound along a ring-shaped trajectory in which an operating section is identified that extends along the maximum length of a log that can be positioned between the two spindles. In the active section, the blade lies in a plane that is substantially tangential to the first rotation axis and that is gradually made to advance towards the first rotation axis in synchronisation with the rotation. In particular, during each turn of the log on itself, the blade is gradually made to advance towards the first rotation axis by a step equal to the thickness of the wood veneer to be obtained.

For peeling machines, just as for many other wood cutting apparatuses, technical solutions have been developed over the years that aim to optimise the value of the wood veneer obtained.

In particular, there are primarily three parameters that can be optimised: the position to be assumed by the first rotation axis relative to the log; the thickness of the veneer (but only if the plant provides for veneers to be made with different thicknesses); and the cut start position. Other possible parameters are the start and end radii for peeling (measured relative to the optimised rotation axis); depending on the quality of the external and internal parts of the log, peeling might only affect a portion of the log itself.

In known plants, the parameters of interest are determined upstream of the peeling machine using known log examination apparatuses.

In some plants, once the optimised parameters have been identified, the logs are tracked as far as the peeling machine, which therefore knows the identity of each log to be processed. In other plants, however, logs are fed to the peeling machine at random and the apparatus does not know the identity of each individual log in advance. Moreover, in either case the peeling machine does not know the angular orientation of the log placed in the loading station. To address all of these unknowns, the peeling apparatuses in the prior art comprise a 3D scanner and an axial rotation device associated with the loading station. Each log placed in the loading station is rotated on itself while the scanner detects its external geometric shape. The virtual model of the log surface is then used either only to understand the angular orientation of the log (by comparing it with a virtual model of the same log acquired when optimising the cutting parameters), or both to recognise the log and to understand its orientation (recognition is performed by comparing the virtual model with previously stored virtual models of known logs).

However, this known technology has some drawbacks.

First, both the recognition of only the angular orientation of the log and the recognition of its identity work well as long as the surface of the log has significant irregularities that can characterise it. Otherwise, when the log has a very regular external surface (as may be the case for some varieties of plants), the shape of the external surface does not allow either the log to be identified or the orientation of a known log to be identified.

In this context, the technical purpose of the present invention is to produce an apparatus for peeling logs that offers a solution to the issues mentioned above.

In particular, the technical purpose of the present invention is to make an apparatus for peeling logs that both allows logs to be recognised and allows their orientation to be identified, even for logs that have a very regular outer surface.

The technical purpose and the aims indicated above are substantially achieved by an apparatus for peeling logs in accordance with the contents of the independent claim enclosed. Other advantages are achieved by the embodiments described in the dependent claims.

Further features and the advantages of the present invention will become more apparent after a careful reading of the detailed description of several preferred, non-limiting embodiments of an apparatus for peeling logs, as shown in the accompanying drawings, in which:

FIG. 1 shows a schematic view from above of some parts of a peeling apparatus according to the present invention, during a first work step;

FIG. 2 shows a side view of a part of the apparatus in FIG. 1, as viewed from the left;

FIG. 3 shows a front view of a part of the apparatus in FIG. 1;

FIG. 4 shows the parts in FIG. 3, in a second work step subsequent to the first work step;

FIG. 11 shows a view from above of a subsequent seventh work step.

Figure 6:
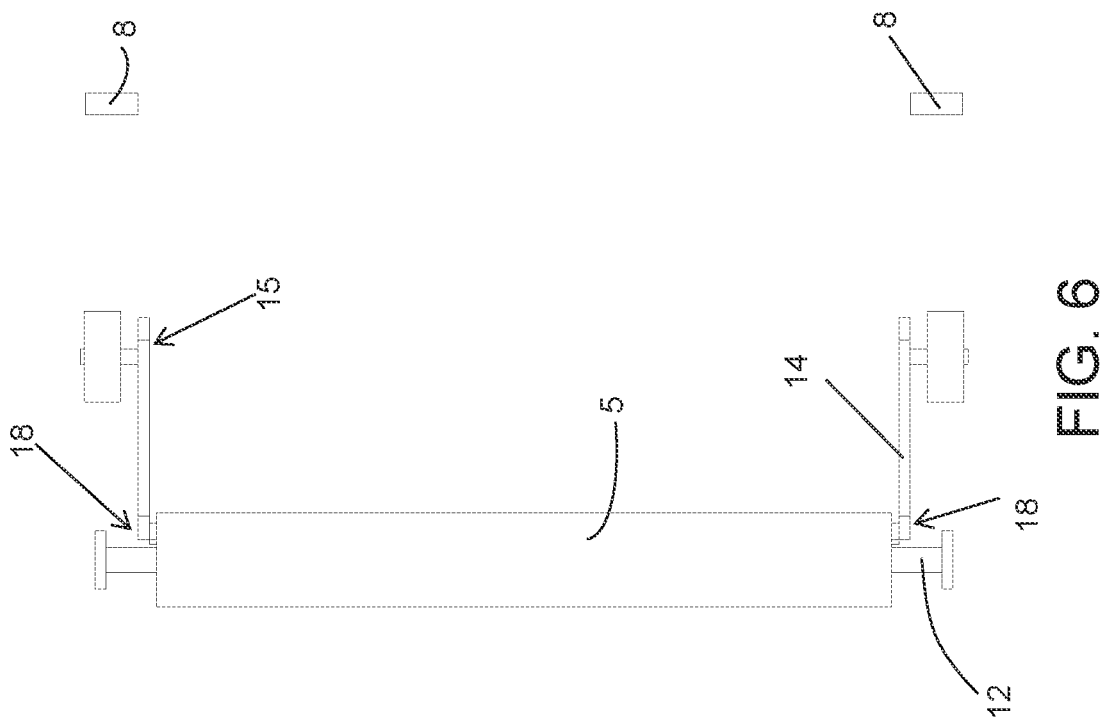
FIG. 6 shows a view from above of the parts in FIG. 5, during a third work step subsequent to the second work step.

Similar to known log peeling apparatuses, the log peeling apparatus 1 described in this invention also comprises three main components: a loading station 2, a cutting station 3 and a device 4 for transferring logs 5 from the loading station 2 to the cutting station 3.

A supporting structure, which may comprise one or more parts, supports the loading station 2, the cutting station 3 and the transfer device 4.

At the loading station 2, the apparatus, in use, receives each log 5 to be peeled, advantageously from a feeding line. The loading station 2 is advantageously configured to receive one log 5 at a time.

In the cutting station 3, a cutting device 6 is present which is configured to, in use, perform a spiral cut of the log 5 while the log 5 is rotated about a first rotation axis 7, similarly as previously envisaged by known peeling apparatuses.

To rotate the logs 5, the cutting station 3 includes a pair of first spindles 8 mounted on the supporting structure. The first spindles 8 are motorised and coaxial relative to the first rotation axis 7. The first spindles 8 are also axially spaced apart and axially movable relative to each other, between a first rest position and a first working position. When in the first rest position, the first spindles 8 are spaced more widely apart than when in the first working position, allowing a log 5 with end faces facing the first spindles 8 to be inserted between them. When in the first working position, the first spindles 8 are configured to axially hold the log 5 by clamping it at the end faces. Furthermore, when in the first working position, the first spindles 8 may rotate about the first rotation axis 7 to rotate the log 5 on itself. Since the peeling apparatus 1 may be used to process logs 5 of different lengths, the first spindles 8 may advantageously assume a plurality of distinct first working positions, each characterised by having a different distance from each other.

The cutting device 6 is mounted on the supporting structure and is operationally associated with the pair of first spindles 8 in order to move relative to them during the rotation of the log 5 about the first rotation axis 7 and, thus, peel the log 5 rotated by the first spindles 8. Just as in known peeling apparatuses, also in that described in the present invention the cutting device 6 advantageously comprises a blade 9 slidable along a ring-shaped trajectory in which an active section can be identified at the log 5. Said active section lies in a plane that is oriented, at least primarily, tangentially relative to the first rotation axis 7 and that is movable relative to the first rotation axis 7 in order to gradually decrease the distance and thus perform the spiral cut.

The cutting station 3, the loading station 2 and the transfer device 4 are associated among each other in such a way as to interact, in use, to position the log 5 in the cutting station 3. In particular, they advantageously interact in such a way as to control the position of the first rotation axis 7 relative to the log 5, preferably by making it coincide with an optimised rotation axis that has been determined for the log 5 itself. In some applications, they may also interact in such a way that the cutting device 6 starts cutting the log 5 at a specific cut start position that has also been previously optimised. Advantageously, the cut start position can be defined with a radial distance relative to the optimised rotation axis, and with an angle of rotation about the optimised rotation axis (in essence, these are polar coordinates expressed relative to a reference system integral with the log 5).

In some embodiments, such as that shown in the accompanying figures, the position of the first rotation axis 7 relative to the supporting structure is fixed, as is the position of the transfer device 4 relative to the cutting station 3. In that case, the interaction enabling the position of the log 5 to be controlled is made between the transfer device 4 and the loading station 2; in particular, the latter will advantageously be able to feed the log 5 into the transfer device 4 in any possible position and orientation.

The loading station 2 comprises a device 10 for axially rotating the log 5, configured to rotate the log 5 about a second rotation axis 11, advantageously parallel to the first rotation axis 7.

In some embodiments, the axial rotation device 10 comprises a pair of second spindles 12 mounted on the supporting structure. The second spindles 12 are entirely analogous to the first spindles 8 in terms of their motion relative to each other and relative to the log 5.

The second spindles 12 are motorised and coaxial relative to the second rotation axis 11. The second spindles 12 are also axially spaced apart and axially movable relative to each other, between a second rest position and a second working position. When in the second rest position, the second spindles 12 are spaced more widely apart than when in the second working position, allowing a log 5 with end faces facing the second spindles 12 to be inserted between them. When in the second working position, the second spindles 12 are configured to axially hold the log 5 by clamping it at the end faces. Furthermore, when in the second working position, the second spindles 12 may rotate about the second rotation axis 11 to rotate the log 5 on itself. Finally, the second spindles 12 may also advantageously assume a plurality of distinct second working positions, each characterised by having a different distance from each other.

Advantageously, the second spindles 12 are mounted on a supporting member 13 that is movable in a plane perpendicular to the second rotation axis 11. This displacement of the supporting member 13 allows a different positioning of the log 5 to be determined relative to the log 5 transfer device 4, as explained in more detail below.

In these applications, the log 5 transfer device 4 is configured to transfer a log 5 by picking it up from the pair of second spindles 12 and releasing it to the pair of first spindles 8.

Preferably, the transfer device 4 comprises two arms 14 that are movable between a pick-up position, at which they are associated with the loading station 2 to pick up a log 5 supported by the second spindles 12, and a release position, at which they are associated with the cutting station 3 to allow the log 5 to be picked up by the first spindles 8. In some embodiments, at one of their secured ends 15, the movable arms 14 are rotatably connected to the supporting structure according to a third rotation axis 17, which is parallel to both to the first rotation axis 7 and the second rotation axis 11, and they may swing between the pick-up and release positions about the third rotation axis 17. In particular, two operational ends 18 of the movable arms 14, which are opposite to the secured ends 15, swing between the two positions. The movable arms 14 are also advantageously movable relative to each other along the third rotation axis 17 in order to bring the operational ends 18 closer to and further away from each other and consequently to jam a log 5 between the operational ends 18 or to release it. In both the pickup position and the release position, the operational ends 18 are also eccentric relative to the second spindles 12 and the first spindles 8, respectively, so that they can freely interact with the log 5.

In these embodiments, the displacement of the supporting member 13 of the second spindles 12 allows a different positioning of the log 5 to be determined relative to the log movable arms 14 placed in the pickup position.

According to one of the innovative aspects of the apparatus described in the present invention, the loading station 2 comprises a radiographic examination device 19, which comprises an x-ray emission unit 20 and an x-ray detection unit 21.

The radiographic examination device 19 is configured to generate, in use, radiographic scans of the log 5. In particular, the radiographic examination device 19 is preferably configured to generate a plurality of radiographic scans of each log 5 as it is rotated about the second rotation axis 11.

The peeling apparatus 1 further comprises an electronic unit (not shown) that is connected at least both to the radiographic examination device 19 to command its activation and receive digital-format data from it relating to each radiographic scan generated by it, and to the axial rotation device 10 of the log 5 to control its operation. Preferably, the electronic unit is connected to all devices of the apparatus in order to monitor and/or control their operation. In preferred embodiments, the electronic unit is an electronic processing and control unit, advantageously comprising one or more computers. The various parts to which it is connected are monitored and controlled by sensors, detectors and interfaces that are of a known type and, therefore, are not discussed here in detail.

In general, the electronic unit is programmed to use the digital-format data from the radiographic scans to control the peeling operations to be performed on the log 5. In practice, this translates to controlling the transfer of the log 5 from the loading station 2 to the cutting station 3 and/or to controlling the operation of the cutting station 3.

Advantageously, in some embodiments (hereinafter referred to as the first operating mode) the electronic unit is programmed to use the digital-format data relating to the radiographic scans to determine, for the log 5 placed in the loading station 2, the position of the optimised rotation axis to be used as the rotation axis in the cutting station 3 (which should therefore be made to coincide with the first rotation axis 7). In addition, it may be programmed to determine an initial angular position to be assumed by the log 5 in the cutting station 3 prior to starting the cutting operations.

The electronic unit is also programmed to control the interaction of the cutting station 3, the loading station 2 and the transfer device 4 in such a way as to control in use the transfer of the log 5 from the loading station 2 to the cutting station 3, positioning each log 5 in the cutting station 3 by having the first rotation axis 7 coincide with the optimised rotation axis.

In some embodiments (hereinafter referred to as the second operating mode), the electronic unit is programmed to use the digital-format data to identify the optimised peeling parameters to be used for cutting the log 5 placed in the loading station 2.

It is also programmed to control the cutting station 3, the loading station 2 and/or the transfer device 4 based on the peeling parameters thus identified. Before delving into the features of the electronic unit, detailed analysis will be given to the radiographic examination device 19.

In some embodiments, the loading station 2 defines an examination space 22 within which, in use, the log 5 placed at the loading station 2 is located. In the context of the present invention, the examination space 22 is considered to coincide with the cylinder that is axially delimited by the second spindles 12 placed in the second working position, wherein they are at the maximum distance from each other, and which has a radius at least equal to the maximum radius of a log 5 processible by the peeling apparatus 1. The length of the examination space 22 will subsequently be defined as its extension parallel to the second rotation axis 11, and the width will be defined as its extension radial to the second rotation axis 11.

The x-ray emission unit 20 and the x-ray detection unit 21 face each other and are positioned on opposite sides of the examination space 22 and of the second axis of rotation 11. In other words, the radiographic scans are performed transversally to the second rotation axis 11.

In some embodiments, the radiographic examination device 19 is configured in such a way that each radiographic scan affects the entire examination space 22; which is to say the entire length of the examination space 22 along the second axis of rotation 11 and the entire width of the examination space 22 perpendicular to the second axis of rotation 11. In this manner, each radiographic scan affects the entire log 5 present in the examination space 22.

In some embodiments, however, the radiographic examination device 19 is configured in such a way that each radiographic scan affects the entire width of the examination space 22 perpendicular to the second axis of rotation 11, but only part of an entire length of the examination space 22 along the second axis of rotation 11. In these embodiments, the radiographic examination device 19 is also advantageously movable relative to the examination space 22, parallel to the second axis of rotation 11, between a first end position and a second end position. When the radiographic examination device 19 is in the first end position, each radiographic scan performed by it affects a first end portion of the examination space 22, whereas when it is in the second end position, each radiographic scan affects a second end portion of the examination space 22 opposite the first end portion. Any portions of the examination space 22 that are not part of the first end portion or the second end portion are affected by the radiographic scans performed by the radiographic examination device 19 at intermediate positions between the first end position and the second end position.

In some embodiments, such as that shown in accompanying FIGS. 1 and 2, the motion of the radiographic examination device 19 relative to the examination space 22 is obtained by moving, simultaneously and in an integral manner, both the x-ray emission unit and the x-ray detection unit along the second rotation axis 11. In other embodiments, however, it may be arranged for only one of the two units to move, provided that the other is configured in such a way as to allow radiographic scans to be made in all positions assumed by the movable unit. By way of example, it may be arranged for an x-ray emitting unit 20 movable along the second axis of rotation 11 to be coupled to a fixed x-ray receiving unit having an axial extension substantially corresponding to at least the length of the examination space 22.

The electronic unit which, as said, is connected to the radiographic examination device 19 to command its activation and receive digital-format data from the radiographic examination device 19 relating to each radiographic scan generated by the radiographic examination device 19, is preferably programmed to command the activation of the radiographic examination device 19 a plurality of times, during the motion of the radiographic examination device 19 from the first end position to the second end position and to receive digital-format data from the radiographic examination device 19 relating to each radiographic scan generated by the radiographic examination device 19 at each of said activations.

Advantageously, the electronic unit is also programmed to move the radiographic examination device 19 from the first end position to the second end position, during the rotation of the log 5 about the second axis of rotation 11 by the axial rotation device 10.

In some embodiments, wherein the electronic unit is connected to the radiographic examination device 19 to command its activation and receive digital-format data from the radiographic examination device 19 relating to each radiographic scan generated by the radiographic examination device 19, the electronic unit is advantageously programmed to command the activation of the radiographic examination device 19 a plurality of times during each rotation of the log 5 about the second axis of rotation 11, to so obtain from the radiographic examination device 19 digital-format data relating to a plurality of radiographic scans of the log 5 executed at a corresponding plurality of different angular positions.

In particular, in the preferred embodiments, the axial rotation device 10, the radiographic examination device 19 and the electronic unit are all also part of a CT scanner 23 that, in turn, forms part of the peeling apparatus 1.

Depending on the use that the electronic unit is programmed to make of the radiographic scans, the number of tomographic scans acquired during the motion of the radiographic examination device 19 and/or during the rotation of the log 5 may vary significantly, and this is also true in the case where the peeling apparatus 1 includes the CT scanner 23 and generates a tomographic model. Indeed, in relation to the latter case, the present invention covers applications with a standard CT scanner 23 capable of performing accurate reconstructions as well as applications in which the CT scanner is of a type configured to perform approximate reconstructions (such as the one described in patent application US 2011/0069811 A1).

In some applications, the electronic unit is also programmed to use the radiographic scan data to generate a fingerprint of the log 5 that will be used to recognise the log 5 and, where appropriate, its orientation. The fingerprint may comprise either a single radiographic scan of the entire log 5 or of a part thereof, or a more or less complete and accurate tomographic model of the log 5 or of a part thereof, or a set of radiographic scans acquired using known orientations of the log 5 relative to the radiographic examination device 19 (advantageously, the relative angular position of the log 5 is always known since the log 5 is mechanically held by the axial rotation device 10 whose actuation is controlled, for example, by the electronic unit). Once the fingerprint is obtained, the electronic unit is further programmed to compare the fingerprint of the log 5 being processed against a plurality of stored fingerprints relating to known logs 5. The purpose of this comparison step is to identify a match between the log 5 being processed and a known log 5 for which either the optimised rotation axis to be used for cutting (according to the first operating mode) or the optimised peeling parameters to be used for cutting (according to the second operating mode) have been previously determined, respectively.

Finally, in the case of the first operating mode, based on the match thus identified, the electronic unit is programmed to identify a current position of the optimised rotation axis previously determined for the known log 5, relative to the log 5 placed in the loading station 2. The position of the optimised rotation axis may be defined relative to the second rotation axis 11 in terms of a (vector) displacement in the plane perpendicular to the second rotation axis 11 (see arrow 16 in FIG. 4).

In the case of the second operating mode, based on the match identified, the electronic unit is programmed to identify the optimised peeling parameters for the log 5 placed in the loading station 2 within the optimised peeling parameters stored in relation to the known log for which the match was identified.

In some embodiments in which the peeling apparatus 1 comprises the CT scanner 23, the electronic unit is also programmed to use the radiographic scan data to generate a virtual tomographic model of the log 5. Subsequently, the electronic unit can be programmed either to determine a fingerprint of the log 5 as described above or to analyse the virtual tomographic model obtained and, from this, determine, respectively, either only the position of the optimised rotation axis to be used to cut the log 5 (according to the first operating mode), or one or more of the rotation axis position, the cut start position, the thickness and the start and end radii for peeling (according to the second operating mode). Optimisation operations using the virtual tomographic model can be performed using known optimisation algorithms as described, for instance, in patent application EP 2202039 A1. Subsequently again, the electronic unit may be programmed to identify a current position of the thus-determined optimised rotation axis relative to the log 5 placed in the loading station 2; which is to say, relative to the second rotation axis 11.

In other embodiments according to the first operating mode, in which the identity of the log 5 is itself known, the electronic unit is programmed to use the radiographic scan data to identify the current position of the previously determined optimised rotation axis relative to the log 5 held by the second spindles 12, and possibly the cut start position.

In some embodiments, the electronic unit is additionally connected to the loading station 2, the cutting station 3 and/or the log 5 transfer device 4 to control their reciprocal movement. In this case, for instance, once the electronic unit has identified the position of the optimised rotation axis relative to the log 5 held by the second spindles 12, and possibly also the cut start position, it is programmed to control their reciprocal movement in such a way that the log 5 transfer device 4 feeds each log 5 into the cutting station 3 by aligning the optimised rotation axis with the first rotation axis 7. To this end, the electronic unit may, for instance, simultaneously control the rotation of the second spindles 12 (or more generally of the axial rotation device 10) and the position of the supporting member 13 to position the log 5 relative to the transfer device 4 placed in the pickup position in such a way that the subsequent movement of the transfer device 4 to the release position brings the log 5 between the first spindles 8 with the optimized rotation axis aligned with the first rotation axis 7. Once the electronic unit has identified the position of the optimised rotation axis relative to the log 5 held by the second spindles 12, and possibly also the cut start position, the apparatus is configured to hold the log 5, which is always mechanically secured and controlled until the end of the cutting procedure.

Advantageously, the loading station 2, the log 5 transfer device 4 and/or the cutting station 3 are reciprocally movable in such a way that the first rotation axis 7 can be positioned in a plurality of different positions relative to the log 5, irrespective of the position that the second rotation axis 11 has relative to the log 5 in the loading station 2. In other words, the loading station 2, the log 5 transfer device 4 and/or the cutting station 3 are configured to position the first rotation axis 7 in a plurality of different positions relative to the log 5 when they position the log 5 in the cutting station 3

The operation of a peeling apparatus 1 made in accordance with the present invention is schematically shown in the attached FIGS. 1 to 11, wherein the peeling apparatus 1 comprises a CT scanner with a movable radiographic examination device 19.

With the second spindles 12 in the second rest position, a log 5 is positioned in the loading station 2. The second spindles 12 are then moved to the second working position, clamping the log 5 between them. Subsequently, the axial rotation device 10 rotates the log 5 on itself in such way that position of the log 5 is known to the electronic unit. As the log 5 rotates, the radiographic examination device 19, if provided, translates from the first end position to the second end position (FIGS. 1, 2 and 3), in the meantime acquiring a plurality of the radiographic scans of the log 5. For each acquisition, the electronic unit also stores the (angular) position of the radiographic examination device 19 relative to the log 5. If the aim is to subsequently reconstruct the virtual tomographic model, the advancement speed of the radiographic examination device 19 and the rotation speed of the log 5 are coordinated in such a way that each portion of the log 5 transversal to the second rotation axis 11 is scanned from a plurality of different angular positions distributed around the rotation axis in such a way as to cover an angle greater than 180° (preferably with a sufficiently small step, for example between 1° and 2°).

Figure 5:
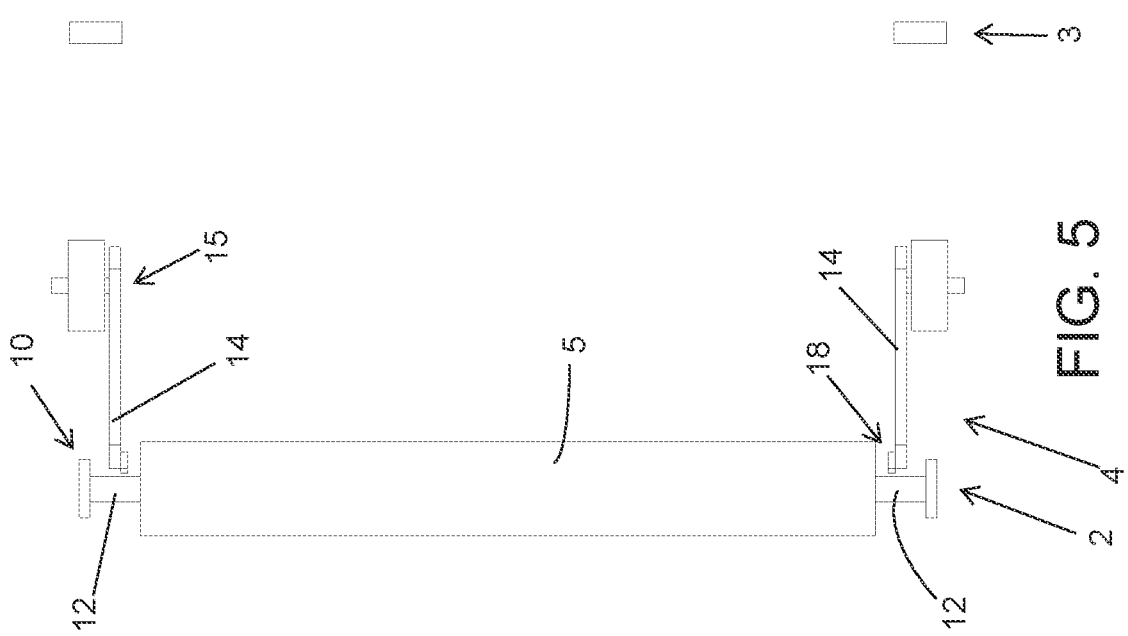
FIG. 5 shows a view from above of some parts of the apparatus in FIG. 1, during the second work step in FIG. 4.

At the end of the radiographic scanning step, the electronic unit identifies the position of the optimised rotation axis relative to the second rotation axis 11 and determines the roto-translation that the log 5 must undergo to be positioned correctly so that it can be subsequently grasped by the transfer device 4. Once both the rotation and translation have been determined, the electronic unit drives the supporting member 13 to translate the log 5 (FIG. 4) and drives the second spindles 12 to rotate it, so positioning it in the correct position between the movable arms 14 of the transfer device 4 placed in the pickup position and spaced apart (FIG. 5).

The movable arms 14 are then brought closer to each other until they jam the log 5 (FIG. 6). At that point, the second spindles 12 move into the second rest position (FIG. 7) and the supporting member 13 can return them to the starting position where they can pick up a new log 5 that is fed into the loading station 2.

Figure 8:
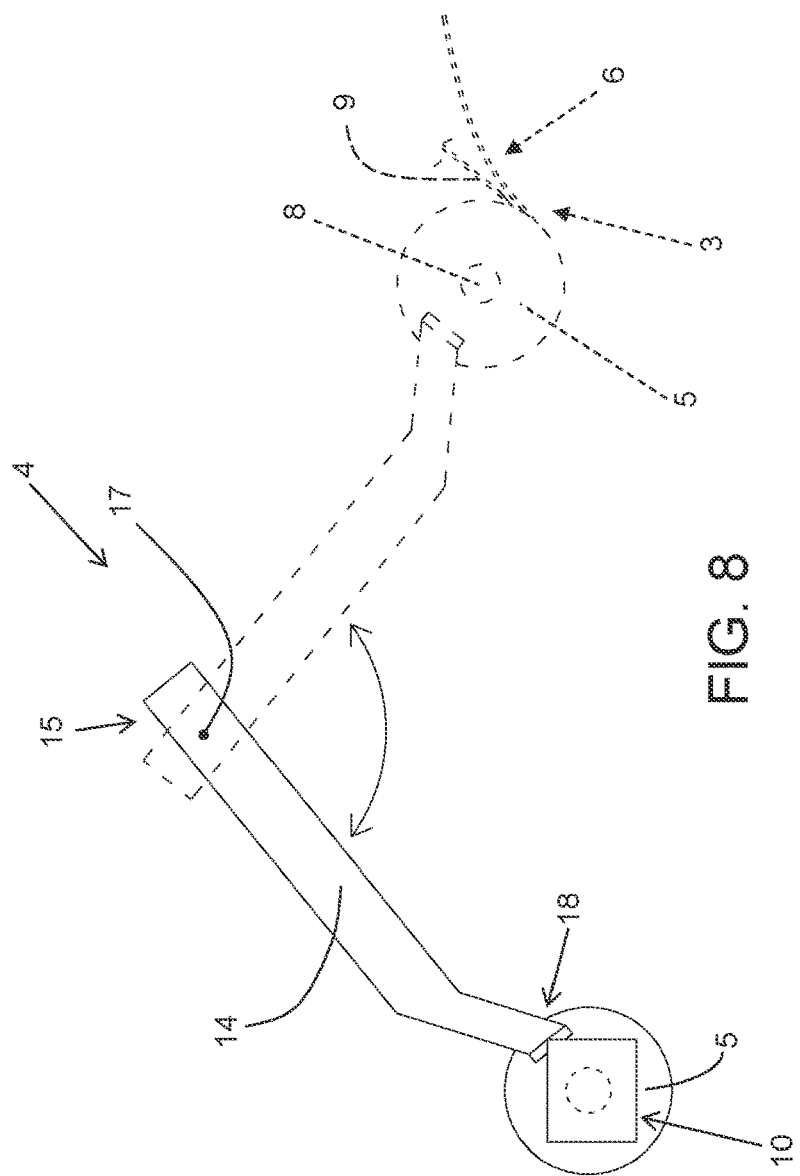
FIG. 8 shows a front view of the starting (continuous line) and end (dashed line) positions of each part in FIG. 7, during a subsequent fifth work step.
Figure 7:
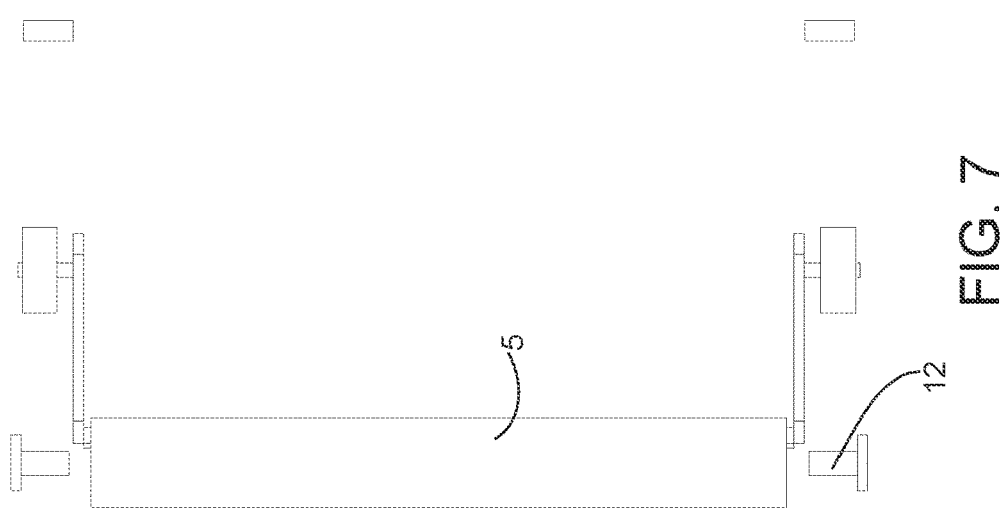
FIG. 7 shows a view from above of the parts in FIG. 6, during a fourth work step subsequent to the third work step.
Figure 10:
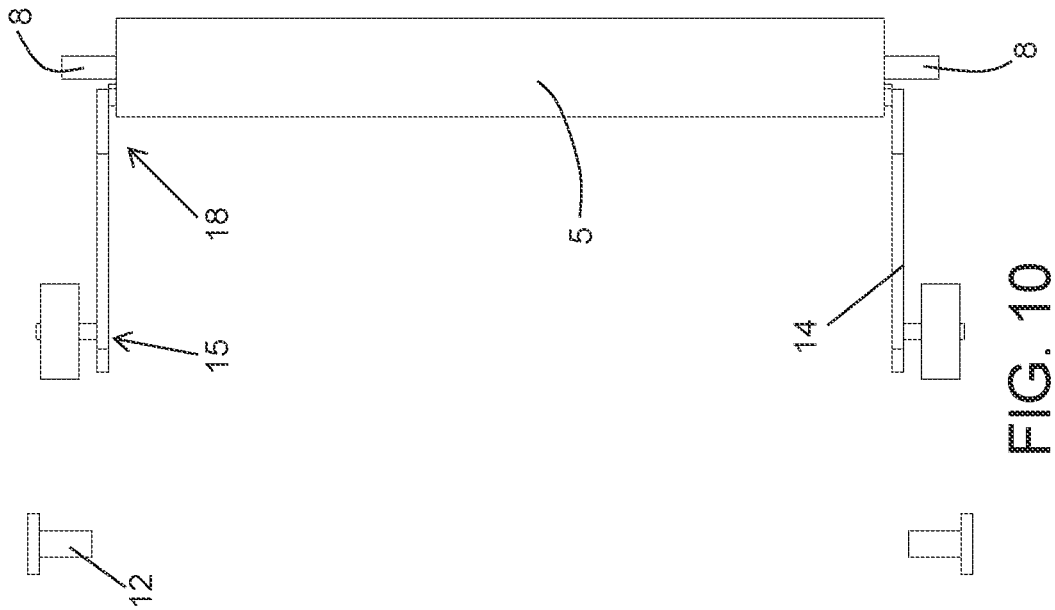
FIG. 10 shows a view from above of a subsequent sixth work step.
Figure 9:
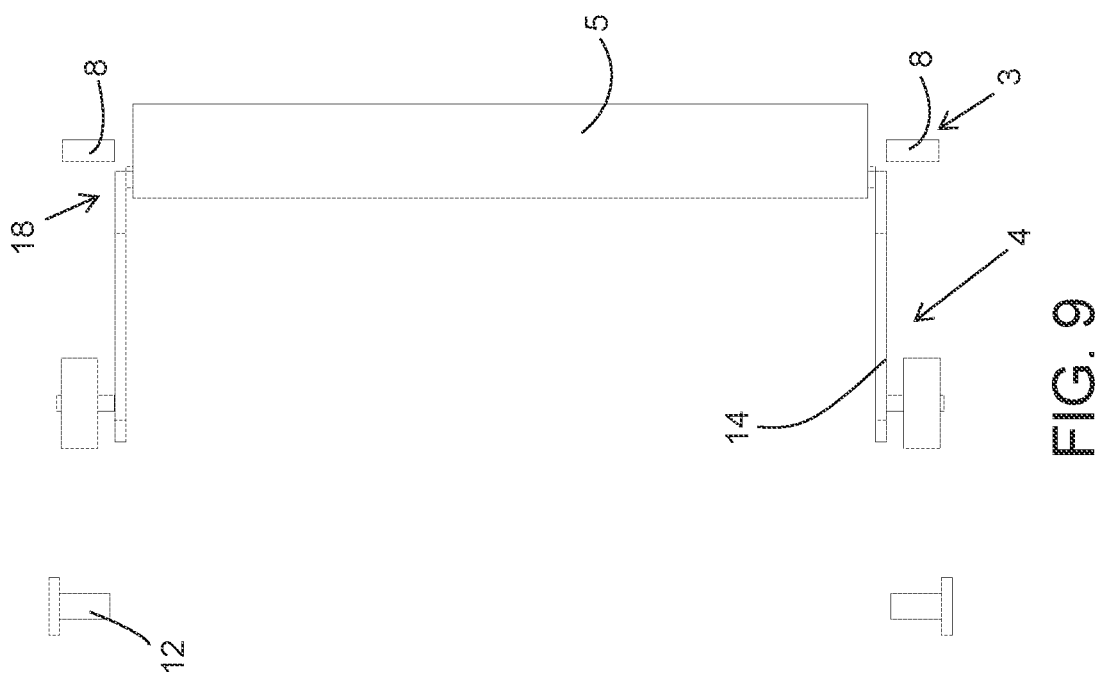
FIG. 9 shows a view from above of the end position in FIG. 8.

The electronic unit activates the transfer device 4, which brings the movable arms 14 from the pickup position to the release position, where the log 5 is positioned between the first spindles 8 placed in the relative first rest position (FIGS. 8 and 9—in FIG. 8, for illustration purposes only, the cutting device 6 is also shown in dashed lines, although at this stage it is not yet activated). The optimised rotation axis is aligned with the rotation axis of the first spindles 8 (which is to say, the first rotation axis 7).

The first spindles 8 switch to the first working position (FIG. 10) and then the movable arms 14 move away to release the log 5.

At that point, the cutting device 6 is brought closer to the rotating log 5 (FIG. 11—possibly in such a way as to start cutting at the predetermined cut start position) and the production of the veneer begins.

The present invention offers significant advantages.

Indeed, the present invention has first of all made it possible to make an apparatus 1 for peeling logs 5 that both allows logs 5 to be recognised and allows their orientation to be identified, even for logs 5 that have a very regular outer surface.

Additionally, in the embodiment in which the apparatus comprises a CT scanner 23, the present invention has made it possible to make an apparatus for peeling 1 logs 5 that does not require upstream equipment to study the log 5 and select the cutting pattern. In fact, all optimisation operations can be carried out directly by the peeling apparatus 1 upon receiving the log 5.

Finally, it is worth noting that the present invention is relatively easy to make and that the cost associated with its implementation is also not very high.

The invention described above may be modified and adapted in several ways without thereby departing from the scope of the inventive concept.

All details can be replaced by other technically equivalent details and any materials, shapes and dimensions of the various components may be used according to requirements.

The invention claimed is:

1. Apparatus for peeling logs (5) comprising:
   a cutting station (3) wherein a cutting device (6) is present configured to perform, in use, a spiral cut of the log (5) while the log (5) is rotated about a first rotation axis (7);
   a loading station (2) at which, in use, the apparatus receives each log (5) to be peeled; and
   a device (4) for transferring logs (5) from the loading station (2) to the cutting station (3);
   wherein:
   the cutting station (3), the loading station (2) and the device (4), in use, interact with each other to position the log (5) in the cutting station (3);
   the loading station (2) includes an axial rotation device (10) configured to rotate the log (5) about a second rotation axis (11);
   the loading station (2) comprises a radiographic examination device (19), comprising an x-ray emission unit (20) and an x-ray detection unit (21), which is configured to generate, in use, radiographic scans of the log (5);
   the apparatus further comprises an electronic unit that is connected to the radiographic examination device (19) to command its activation and receive digital-format data from it relating to each radiographic scan generated by it, as well as to the axial rotation device (10) of the log (5) to control its operation;
   and wherein:
   the electronic unit is programmed to use said digital-format data to control a transfer of the log (5) from the loading station (2) to the cutting station (3) and/or to control the operation of the cutting station (3);
   the loading station (2) defines an examination space (22) within which, in use, the log (5) placed at the loading station (2) is located, and wherein the x-ray emission unit (20) and the x-ray detection unit (21) face each other and are positioned on opposite sides of the examination space (22) and of the second axis of rotation (11);
   the radiographic examination device (19) is configured in such a way that each radiographic scan affects an entire width of the examination space (22) perpendicular to the second rotation axis (11) and only part of an entire length of the examination space (22) along the second rotation axis (11); and
   the radiographic examination device (19) is movable relative to the examination space (22), parallel to the second axis of rotation (11), between a first end position at which each radiographic scan affects a first end portion of the examination space (22) and a second end position at which each radiographic scan affects a second end portion of the examination space (22) opposite the first end portion.

2. Apparatus according to claim 1, wherein the motion of the radiographic examination device (19) relative to the examination space (22) is obtained by moving either the x-ray emission unit or the x-ray detection unit, or both, along the second rotation axis (11).

3. Apparatus according to claim 1 wherein the electronic unit is programmed to move the radiographic examination device (19) from the first end position to the second end position during the rotation of the log (5) about the second axis of rotation (11) by the axial rotation device (10).

4. Apparatus according to claim 1 wherein the electronic unit, which is connected to the radiographic examination device (19) to command its activation and receive digital-format data from the radiographic examination device (19) relating to each radiographic scan generated by the radiographic examination device (19), is further programmed to command the activation of the radiographic examination device (19) a plurality of times, during the motion of the radiographic examination device (19) from the first end position to the second end position and to receive digital-format data from the radiographic examination device (19)

relating to each radiographic scan generated by the radiographic examination device (19) at each of said activations.

5. Apparatus according to claim 1, wherein the electronic unit, which is connected to the radiographic examination device (19) to command its activation and receive digital-format data from the radiographic examination device (19) relating to each radiographic scan generated by the radiographic examination device (19), is further programmed to command the activation of the radiographic examination device (19) a plurality of times during each rotation of the log (5) about the second axis of rotation (11), to so obtain from the radiographic examination device (19) digital-format data relating to a plurality of radiographic scans of the log (5) executed at a plurality of different angular positions.

6. Apparatus according to claim 1, further comprising a CT scanner (23) that comprises the axial rotation device (10), the radiographic examination device (19) and the electronic unit.

7. Apparatus according to claim 1, wherein the loading station (2), the log (5) transfer device (4) and/or the cutting station (3) are reciprocally movable and are configured for being able to position the first rotation axis (7) in a plurality of different positions relative to the log (5), irrespective of the position that the second rotation axis (11) has relative to the log (5) in the loading station (2).

8. Apparatus according to claim 1, wherein the electronic unit is further programmed to use said digital-format data to determine a position of an optimised rotation axis of the log (5) placed in the loading station (2) and to control, in use, the interaction of the cutting station (3), the loading station (2) and the transfer device (4) to control the transfer of the log (5) from the loading station (2) to the cutting station (3) and to position the log (5) in the cutting station (3) by having the first rotation axis (7) coincide with the optimised rotation axis.

9. Apparatus according to claim 8, wherein the electronic unit is further programmed to:
use the radiographic scan data to generate a fingerprint of the log (5);
compare the fingerprint of the log (5) against a plurality of stored fingerprints of known logs (5) for which an optimised rotation axis to be used for cutting has been previously determined, to identify a match between the log (5) and a known log (5); and
based on the match identified, identify a current position of the previously determined optimised rotation axis relative to the log (5) placed in the loading station (2).

10. Apparatus according to claim 8, wherein the electronic unit is further programmed to:
use the radiographic scan data to generate a virtual tomographic model of the log (5);
from the virtual tomographic model, determine an optimised rotation axis to be used for cutting the log (5); and
identify a current position of the thus-determined optimised rotation axis relative to the log (5) placed in the loading station (2).

11. Apparatus according to claim 8, wherein the electronic unit is further programmed to use the radiographic scan data to identify a current position of a previously determined optimised rotation axis to be used for cutting the log (5), relative to the loading station (2).

12. Apparatus according to claim 7, wherein the electronic unit is further programmed to:
use the radiographic scan data to generate a fingerprint of the log (5);
compare the fingerprint of the log (5) against a plurality of stored fingerprints of known logs (5) for which an optimised rotation axis to be used for cutting has been previously determined, to identify a match between the log (5) and a known log (5); and
based on the match identified, identify a current position of the previously determined optimised rotation axis relative to the log (5) placed in the loading station (2);
and wherein the electronic unit is additionally connected to the loading station (2), the cutting station (3) and/or the log (5) transfer device (4) to control their reciprocal movement in such a way that the log (5) transfer device (4) feeds each log (5) into the cutting station (3) by aligning the optimised rotation axis with the first rotation axis (7).

13. Apparatus according to claim 1, wherein the electronic unit is further programmed to use said digital-format data to identify optimised peeling parameters to be used for cutting the log (5) placed in the loading station (2) and to control the cutting station (3), the loading station (2) and/or the transfer device (4) based on the peeling parameters thus identified.

14. Apparatus according to claim 13, wherein the electronic unit is further programmed to:
use the radiographic scan data to generate a fingerprint of the log (5);
compare the fingerprint of the log (5) against a plurality of stored fingerprints of known logs (5) for which optimised peeling parameters to be used for cutting have been previously determined, to identify a match between the log (5) and a known log (5); and
based on the match identified, identify the optimised peeling parameters for the log (5) placed in the loading station (2) within the optimised peeling parameters stored in relation to the known log (5) for which the match was identified.

15. Apparatus according to claim 13, wherein the electronic unit is further programmed to:
use the radiographic scan data to generate a virtual tomographic model of the log (5);
from the virtual tomographic model, determine the optimised peeling parameters for the log (5) placed in the loading station (2).

16. Apparatus according to claim 1 wherein the cutting station (3) comprises a pair of first spindles (8), wherein the first spindles (8) are motorised, coaxial relative to the first rotation axis (7), axially spaced apart and axially movable relative to each other between a first rest position and a first working position, wherein, in the first rest position, the first spindles (8) are more spaced apart than when in the first working position, and wherein the first spindles (8) are configured to axially hold a log (5) and rotate it on itself about the first axis of rotation (7) when in the first working position.

17. Apparatus according to claim 16 wherein the cutting device (6) is operatively associated with the pair of first spindles (8) in order to move relative to them during the rotation of the log (5) about the first rotation axis (7) and, thus, peel the log (5) rotated by the first spindles (8).

18. Apparatus according to claim 1 wherein the axial rotation device (10) comprises a pair of second spindles (12), wherein the second spindles (12) are motorised, coaxial relative to the second rotation axis (11), axially spaced apart and axially movable relative to each other between a second rest position and a second working position, wherein, in the second rest position, the second spindles (12) are more spaced apart than when in the second working position, and wherein the second spindles (12) are configured to axially hold a log (5) and rotate it on itself about the second axis of rotation (11) when in the second working position.

19. Apparatus according to claim 16, wherein the axial rotation device (10) comprises a pair of second spindles (12), wherein the second spindles (12) are motorised, coaxial relative to the second rotation axis (11), axially spaced apart and axially movable relative to each other between a second rest position and a second working position, wherein, in the second rest position, the second spindles (12) are more spaced apart than when in the second working position, and wherein the second spindles (12) are configured to axially hold a log (5) and rotate it on itself about the second axis of rotation (11) when in the second working position; and wherein the log (5) transfer device (4) is configured to transfer a log (5) from the pair of second spindles (12), to the pair of first spindles (8).

20. Apparatus according to claim 19, wherein the transfer device (4) comprises two arms (14) movable between a pick-up position, at which they are associated with the loading station (2) to pick up a log (5) supported by the second spindles (12), and a release position, at which they are associated with the cutting station (3) to allow the log (5) to be picked up by the first spindles (8), and wherein the second spindles (12) are mounted on a supporting body (13) which is movable in a plane perpendicular to the second rotation axis (11), the displacement of the supporting member (13) resulting in a different positioning of the log (5) relative to the movable arms (14) placed in the pick-up position.

21. Apparatus for peeling logs (5) comprising:
a cutting station (3) wherein a cutting device (6) is present configured to perform, in use, a spiral cut of the log (5) while the log (5) is rotated about a first rotation axis (7);
a loading station (2) at which, in use, the apparatus receives each log (5) to be peeled; and
a device (4) for transferring logs (5) from the loading station (2) to the cutting station (3);
wherein:
the cutting station (3), the loading station (2) and the transfer device (4), in use, interact with each other to position the log (5) in the cutting station (3);
the loading station (2) includes an axial rotation device (10) configured to rotate the log (5) about a second rotation axis (11);
the loading station (2) comprises a radiographic examination device (19), comprising an x-ray emission unit (20) and an x-ray detection unit (21), which is configured to generate, in use, radiographic scans of the log (5);
the apparatus further comprises an electronic unit that is connected to the radiographic examination device (19) to command its activation and receive digital-format data from it relating to each radiographic scan generated by it, as well as to the axial rotation device (10) of the log (5) to control its operation;
the electronic unit is programmed to use said digital-format data to control a transfer of the log (5) from the loading station (2) to the cutting station (3) and/or to control the operation of the cutting station (3); and
the electronic unit is further programmed to use said digital-format data to determine a position of an optimised rotation axis of the log (5) placed in the loading station (2) and to control, in use, the interaction of the cutting station (3), the loading station (2) and the transfer device (4) to control the transfer of the log (5) from the loading station (2) to the cutting station (3) and to position the log (5) in the cutting station (3) by having the first rotation axis (7) coincide with the optimised rotation axis;
and wherein the electronic unit is further programmed to:
use the radiographic scan data to generate a fingerprint of the log (5);
compare the fingerprint of the log (5) against a plurality of stored fingerprints of known logs (5) for which an optimised rotation axis to be used for cutting has been previously determined, to identify a match between the log (5) and a known log (5); and
based on the match identified, identify a current position of the previously determined optimised rotation axis relative to the log (5) placed in the loading station (2).

22. Apparatus according to claim 21, wherein the loading station (2) defines an examination space (22) within which, in use, the log (5) placed at the loading station (2) is located, and wherein the x-ray emission unit (20) and the x-ray detection unit (21) face each other and are positioned on opposite sides of the examination space (22) and of the second axis of rotation (11) and wherein the radiographic examination device (19) is configured in such a way that each radiographic scan affects an entire width of the examination space (22) perpendicular to the second rotation axis (11) and either an entire length of the examination space (22) along the second rotation axis (11) only part of the entire length of the examination space (22) along the second rotation axis (11).

23. Apparatus according to claim 21, wherein the electronic unit, which is connected to the radiographic examination device (19) to command its activation and receive digital-format data from the radiographic examination device (19) relating to each radiographic scan generated by the radiographic examination device (19), is further programmed to command the activation of the radiographic examination device (19) a plurality of times during each rotation of the log (5) about the second axis of rotation (11), to so obtain from the radiographic examination device (19) digital-format data relating to a plurality of radiographic scans of the log (5) executed at a plurality of different angular positions.

24. Apparatus according to claim 21, further comprising a CT scanner (23) that comprises the axial rotation device (10), the radiographic examination device (19) and the electronic unit.

25. Apparatus according to claim 21, wherein the loading station (2), the log (5) transfer device (4) and/or the cutting station (3) are reciprocally movable and are configured for being able to position the first rotation axis (7) in a plurality of different positions relative to the log (5), irrespective of the position that the second rotation axis (11) has relative to the log (5) in the loading station (2).

26. Apparatus according to claim 21, wherein the electronic unit is additionally connected to the loading station (2), the cutting station (3) and/or the log (5) transfer device (4) to control their reciprocal movement in such a way that the log (5) transfer device (4) feeds each log (5) into the cutting station (3) by aligning the optimised rotation axis with the first rotation axis (7).

27. Apparatus according to claim 21 wherein the cutting station (3) comprises a pair of first spindles (8), wherein the first spindles (8) are motorised, coaxial relative to the first rotation axis (7), axially spaced apart and axially movable relative to each other between a first rest position and a first working position, wherein, in the first rest position, the first spindles (8) are more spaced apart than when in the first working position, and wherein the first spindles (8) are configured to axially hold a log (5) and rotate it on itself about the first axis of rotation (7) when in the first working position.

28. Apparatus according to claim 21 wherein the axial rotation device (10) comprises a pair of second spindles (12), wherein the second spindles (12) are motorised, coaxial relative to the second rotation axis (11), axially spaced apart and axially movable relative to each other between a second rest position and a second working position, wherein, in the second rest position, the second spindles (12) are more spaced apart than when in the second working position, and wherein the second spindles (12) are configured to axially hold a log (5) and rotate it on itself about the second axis of rotation (11) when in the second working position.

29. Apparatus for peeling logs (5) comprising:
a cutting station (3) wherein a cutting device (6) is present configured to perform, in use, a spiral cut of the log (5) while the log (5) is rotated about a first rotation axis (7);
a loading station (2) at which, in use, the apparatus receives each log (5) to be peeled; and
a device (4) for transferring logs (5) from the loading station (2) to the cutting station (3);
wherein:
the cutting station (3), the loading station (2) and the transfer device (4), in use, interact with each other to position the log (5) in the cutting station (3);
the loading station (2) includes an axial rotation device (10) configured to rotate the log (5) about a second rotation axis (11);
the loading station (2) comprises a radiographic examination device (19), comprising an x-ray emission unit (20) and an x-ray detection unit (21), which is configured to generate, in use, radiographic scans of the log (5);
the apparatus further comprises an electronic unit that is connected to the radiographic examination device (19) to command its activation and receive digital-format data from it relating to each radiographic scan generated by it, as well as to the axial rotation device (10) of the log (5) to control its operation;
the electronic unit is programmed to use said digital-format data to identify optimised peeling parameters to be used for cutting the log (5) placed in the loading station (2) and to control the cutting station (3), the loading station (2) and/or the transfer device (4) based on the peeling parameters thus identified;
and wherein the electronic unit is further programmed to:
use the radiographic scan data to generate a fingerprint of the log (5);
compare the fingerprint of the log (5) against a plurality of stored fingerprints of known logs (5) for which optimised peeling parameters to be used for cutting have been previously determined, to identify a match between the log (5) and a known log (5); and
based on the match identified, identify the optimised peeling parameters for the log (5) placed in the loading station (2) within the optimised peeling parameters stored in relation to the known log (5) for which the match was identified.

30. Apparatus according to claim 29, wherein the loading station (2) defines an examination space (22) within which, in use, the log (5) placed at the loading station (2) is located, and wherein the x-ray emission unit (20) and the x-ray detection unit (21) face each other and are positioned on opposite sides of the examination space (22) and of the second axis of rotation (11) and wherein the radiographic examination device (19) is configured in such a way that each radiographic scan affects an entire width of the examination space (22) perpendicular to the second rotation axis (11) and either an entire length of the examination space (22) along the second rotation axis (11) only part of the entire length of the examination space (22) along the second rotation axis (11).

31. Apparatus according to claim 29, wherein the electronic unit, which is connected to the radiographic examination device (19) to command its activation and receive digital-format data from the radiographic examination device (19) relating to each radiographic scan generated by the radiographic examination device (19), is further programmed to command the activation of the radiographic examination device (19) a plurality of times during each rotation of the log (5) about the second axis of rotation (11), to so obtain from the radiographic examination device (19) digital-format data relating to a plurality of radiographic scans of the log (5) executed at a plurality of different angular positions.

32. Apparatus according to claim 29, further comprising a CT scanner (23) that comprises the axial rotation device (10), the radiographic examination device (19) and the electronic unit.

33. Apparatus according to claim 29, wherein the loading station (2), the log (5) transfer device (4) and/or the cutting station (3) are reciprocally movable and are configured for being able to position the first rotation axis (7) in a plurality of different positions relative to the log (5), irrespective of the position that the second rotation axis (11) has relative to the log (5) in the loading station (2).

34. Apparatus according to claim 29, wherein the electronic unit is further programmed to use said digital-format data to determine a position of an optimised rotation axis of the log (5) placed in the loading station (2) and to control, in use, the interaction of the cutting station (3), the loading station (2) and the transfer device (4) to control the transfer of the log (5) from the loading station (2) to the cutting station (3) and to position the log (5) in the cutting station (3) by having the first rotation axis (7) coincide with the optimised rotation axis.

35. Apparatus according to claim 29 wherein the cutting station (3) comprises a pair of first spindles (8), wherein the first spindles (8) are motorised, coaxial relative to the first rotation axis (7), axially spaced apart and axially movable relative to each other between a first rest position and a first working position, wherein, in the first rest position, the first spindles (8) are more spaced apart than when in the first working position, and wherein the first spindles (8) are configured to axially hold a log (5) and rotate it on itself about the first axis of rotation (7) when in the first working position.

36. Apparatus according to claim 29 wherein the axial rotation device (10) comprises a pair of second spindles (12), wherein the second spindles (12) are motorised, coaxial relative to the second rotation axis (11), axially spaced apart and axially movable relative to each other between a second rest position and a second working position, wherein, in the second rest position, the second spindles (12) are more spaced apart than when in the second working position, and wherein the second spindles (12) are configured to axially hold a log (5) and rotate it on itself about the second axis of rotation (11) when in the second working position.

* * * * *